United States Patent [19]

Ehrenpreis

[11] Patent Number: 4,730,007

[45] Date of Patent: Mar. 8, 1988

[54] NOVEL ANALGESIC COMPOSITIONS

[76] Inventor: Seymour Ehrenpreis, 4339 Birchwood Ave., Skokie, Ill. 60076

[21] Appl. No.: 772,551

[22] Filed: Sep. 4, 1985

[51] Int. Cl.$^4$ .................. A61U 31/16; A61U 31/195
[52] U.S. Cl. ................................ 514/561; 514/629
[58] Field of Search ............................. 514/561, 629

[56] References Cited

PUBLICATIONS

Chem. Abst. 94–(1981)–114234a (Deshpande).
Chem. Abst. 83–(1975)–120870u (McLean).
Chem. Abst. 83–(1975)–120778v (Kovach).

Primary Examiner—Stanley J. Friedman
Attorney, Agent, or Firm—Eugene F. Friedman

[57] ABSTRACT

An analgesic composition comprising an effective amount of an analgesic, anti-inflammatory agent selected from the group consisting of D-phenylalanine, DL-phenylalanine, D-leucine, DL-leucine and hydrocinnamic acid and a synergistically effective amount of acetaminophen is provided by the present invention.

8 Claims, No Drawings

NOVEL ANALGESIC COMPOSITIONS

BACKGROUND OF THE INVENTION

A. Field of the Invention

The present invention relates to analgesic compositions and more specifically relates to synergistic combinations of acetaminophen and an analgesic, anti-inflammatory agent selected from the group consisting of D-phenylalanine, DL-phenylalanine, D-leucine, DL-leucine and hydrocinnamic acid.

Acetaminophen is a well know, and widely used analgesic and antipyretic agent, sold by various companies under the trade marks "Tylenol", "Datril", "Panedol", "Anacin-3", etc. It is currently estimated that McNeil's Tylenol brand of acetaminophen accounts for approximately 30% of the over-the-counter analgesic market.

While aspirin is widely used for the relief of pain, fever and inflammation, and is considered to be the model for non-steroidal anti-inflammatory agents, many people are unable to take aspirin because of its gastrointestinal side effects, and others are unable to take the drug because of sensitivity or allergic reactions. In particular, patients suffering from upper gastrointestinal disorders such as ulcers, gastritis and hiatus hernia, inflammatory bowel disease such as ulcerative colitis, or who exhibit hemostatic disturbances (including anticoagulant therapy), or suffer from asthma, or who have exhibited a sensitivity to aspirin, must take acetaminophen for the relief of mild pain to moderate pain and fever. In addition, in view of the suggested link between aspirin and Reyes syndrome in children, it is generally considered to be unsafe to give a child aspirin to reduce a fever due to cold or flu. Thus, acetaminophen has become an increasingly popular analgesic, anti-pyretic agent both in children and adults because of its' lack of side effects generally associated with aspirin.

While this valuable therapeutic agent has rarely been found to produce any side effects, it has several drawbacks. First, it does not exhibit anti-inflammatory activity, and thus does not relieve inflammation associated with arthritis and other inflammatory conditions, although it is used to relieve pain where aspirin and other non-steroidal anti-inflammatory agents can not be tolerated.

Further, large doses of acetaminophen have been associated with hepatic toxicity, and daily dosages are generally limited to one or two capsules containing 325–500 mg of acetaminophen every four to six hours, and a maximum total daily dosage of 4,000 mg.

While acetaminophen is suitable for controlling mild pain, it generally is not effective in cases of acute or chronic moderate to severe pain associated with oral or other surgery, chronic back pain, cancer, and the like. In such cases, controlled drugs such as codeine alone or in combination with aspirin or acetominophen, or Darvon (propoxyphene), Demerol, morphine, and the like are generally employed. Because of the abuse potential of the control drugs, or narcotics, as well as the undesirable side effects associated therewith, there has been a longstanding need to provide improved analgesic agents which are as safe as acetaminophen, but which have enhanced analgesic properties.

In recent years, an entirely new class of analgesic, anti-inflammatory agents has been reported. Those agents are D-phenylalanine, D-leucine and hydrocinnamic acid. The compounds have are relatively non-toxic, with $LD_1 > 10$ grams/kg in mice, and provide substantial relief from mild to moderate pain.

The analgesic activity of D-phenylalanine, D-leucine and hydrocinnamic acid is potentiated when those agents are co-administered with aspirin or other non-steroidal anti-inflammatory agent. However, this combination therapy is not suitable for patients who can not tolerate aspirin or other non-steroidal anti-inflammatory agents, and that a need therefore exists for analgesic agents which can be employed to treat acute or chronic moderate to severe pain, and which does not suffer from the side effects of aspirin and other non-steroidal anti-inflammatory agents, nor has the side effects and liabilities associated with narcotic analgesic agents. The present invention fulfills that need.

B. Prior Art

D-phenylalanine, DL-phenylalanine, D-leucine, DL-leucine and hydrocinnamic acid have been found to possess analgesic and anti-inflammatory activity. Their analgesic activity is significantly enhanced or potentiated by the co-administration of a prostaglandin synthetase inhibitor selected from the group consisting of aspirin or other non-steroidal anti-inflammatory, antipyretic agents such as ibuprofen and the like. See U.S. Pat. No. 4,439,452, issued Mar. 27, 1984 and commonly assigned, copending applications U.S. Ser. No. 657,681 filed Oct. 4, 1984 and U.S. Ser. No. 657,732, filed Oct. 4, 1984.

D-phenylalanine has also been reported to be useful in the treatment of depression at dosages of 50 or 100 mg per day and has been sold under the trademark "Deprenon" for the treatment of depression. See "Therapy of Depression by Phenylalanine" *Arzneim Forsch*, Vol. 25, NR1 (1975), and "Use of D-Phenylalanine in Parkinson's Disease, *Arzneim Forsch*, Vol. 26, NR4 (1976).

L-leucine and L-phenylalanine are also known to be useful as nutrients.

It has now surprisingly been found that while acetaminophen is not a peripheral prostaglandin synthetase inhibitor nor a non-steroidal anti-inflammatory, antipyretic agent, a synergistic analgesic effect is obtained when acetaminophen is coadministered with a compound selected from the group consisting of D-phenylalanine, DL-phenylalanine, D-leucine, DL-leucine and hydrocinnamic acid.

SUMMARY

The present invention provides compositions which are useful in the treatment of pain and/or inflammation comprising a synergistically effective amount of acetaminophen and an analgesic, anti-inflammatory agent selected from the group consisting of D-phenylalanine, DL-phenylalanine, D-leucine, DL-leucine and hydrocinnamic acid.

DETAILED DESCRIPTION OF PREFERRED EMBODIMENTS

The compositions of the present invention preferably contain from 100 to 500 mg per dose of acetaminophen in combination with from 100–750 mg/dose of D-phenylalanine, D-leucine or hydrocinnamic acid.

The compositions of the present invention are oral dosage forms and include capsules, tablets, syrups, elixirs, and the like. Such compositions may include pharmaceutically acceptable carriers. Solid carriers such as starch, sugars, talc and the like can be used to form powders which may be used for direct administration or to fill gelatin capsules. Suitable lubricants such as magnesium stearate, stearic acid and talc, as well as binders and disintegrating agents may additionally be included to form tablets. Flavoring and sweetening agents may also be added.

Unit dosage forms such as tablets and capsules can contain any suitable, predetermined, therapeutically effective amount of acetaminophen and one or more of the anti-inflammatory, analgesic agents and a pharmaceutically acceptable carrier or diluent.

Liquid oral dosage forms include emulsions, suspensions, solutions, syrups and the like containing diluents commonly used in the art such as water. Besides inert diluents, such preparations can also include adjuvants such as wetting agents, emulsifying and suspending agents, and sweeting, flavoring and perfuming agents.

The amount of active ingredients may be varied; however, it is necessary that the amount of active ingredient be such that a suitable dosage is given. The selected dosage will depend upon the severity and duration of the pain, and the patient response.

D-phenylalanine is the preferred analgesic, anti-inflammatory agent for use in the practice of this invention. It will be understood that when DL-phenylalanine (or DL-leucine) is employed, twice as much material must be employed as when the D-form is administered alone.

The analgesic compositions are administered to a patient in need of such treatment in divided dosages, i.e. three or four times daily, depending upon the severity of the pain.

The preferred potentiating agent is D-phenylalanine. Genenerally speaking, dosages of from 800–1000 mg per day of D-phenylalanine in four equal divided doses of from 200–250 mg have been found to be effective in controlling moderate to severe pain associated with whiplash, lower back pain, migraine and arthritis. The presently preferred compositions accordingly comprise suitable levels of D-phenylalanine and a synergistically effective amount of acetaminophen.

The following examples further illustrate the present invention.

EXAMPLE 1

Analgesic Potency As Determined by the Hot Plate Method

The analgesic activity of D-phenylalanine, D-leucine, hydrocinnamic acid and acetaminophen was measured in the standard mouse hot plate test using metal hot plate maintained at 55° C. The "control" for the hot plate test was determined by placing an untreated mouse on the heated plate and noting the time it takes the untreated or "control" mouse to jump after being placed on the plate. Test and control mice were tested after a single injection of drug or saline respectively for two hours at 30 minute intervals and also 24 hours after the initial injection. Groups of ten (10) mice were tested with each dose of injected substance. A "highly significant" analgesic effect is demonstrated by a time lapse, before the mouse jumps, constituting an increase of 2 to 4 fold over that of control.

Control mice were injected with saline, and test mice received 125 mg/kg of D-phenylalanine or D-leucine or 50 mg/kg of hydrocinnamic acid. For combination experiments, a series of mice first received acetaminophen and were tested by the hot plate method. 60 Minutes later, either 125 mg/kg of D-phenylalanine or D-leucine, or 50 mg/kg of hydrocinnamic acid was administered and the animals tested for another two hours. Other animals were injected with D-phenylalanine, D-leucine or hydrocinnamic acid at these same doses and examined for analgesic activity in the same manner as the animals receiving the combination, i.e., the drug plus acetaminophen. summarized in Table I.

TABLE 1

| Time after administration of acetominophen or saline (hr) | Net Medium Jumping Time, seconds | | |
|---|---|---|---|
| | DPA | DPA + Acetaminophen | % increase |
| 1 | 3.3 | 13.3 | 440 |
| 2 | 2.9 | 5.7 | 203 |
| 24 | 7.0 | 11.8 | 168 |
| | D-leu | D-leu + Acetaminophen | % increase |
| 1 | 2.1 | 3.1 | 148 |
| 2 | 3.9 | 3.8 | 0 |
| 24 | 0 | 0 | 0 |
| | HCA | HCA + Acetaminophen | % increase |
| 1 | 4.0 | 13.3 | 339 |
| 2 | — | — | — |
| 24 | 6.7 | 14.5 | 276 |

D = D-phenylalanine;
D-leu = D-leucine;
HCA = hydrocinnamic acid

As can be seen from the above data, acetaminophen and D-phenylalanine, L-phenylalanine and hydrocinnamic acid each exhibit some analgesic activity at the very low doses used, coadministration of acetaminophen with either D-phenylalanine, D-leucine or hydrocinnamic acid produced a significant, synergistic increase in analgesia.

A major benefit of the present invention is that lower dosages of acetaminophen can be administed to achieve the same effect as currently obtained with the conventional dosages, thus reducing the possible potential of risk of hepatic toxicity in patients suffering from chronic pain.

EXAMPLE 2

Tablets weighing 500 mg and containing 150 mg each of acetaminophen and D-phenylalanine are prepared from the following formulation:

| Ingredient | Amount (Kg) |
|---|---|
| Acetaminophen | 100 |
| D-Phenylalanine | 200 |
| Lactose, U.S.P. | 100 |
| Corn starch, U.S.P. | 85 |
| Talc | 5 |
| Stearic acid | 10 |
| Methanol | 300 ml |

The above ingredients are blended, dried, seived and compressed into tablets.

EXAMPLE 3

Tablets weighing 705 mg are prepared having the following composition:

| Ingredient | Mg/Tablet |
|---|---|
| D-phenylalanine | 250 |
| Acetominophen | 250 |
| Lactose, U.S.P | 200 |

-continued

| Ingredient | Mg/Tablet |
| --- | --- |
| Stearic acid | 5 |

The invention claimed is:

1. An analgesic composition comprising an effective amount of an analgesic, anti-inflammatory agent selected from the group consisting of D-phenylalanine, DL-phenylalanine, D-leucine and DL-leucine and a synergistically effective amount of acetominophen.

2. The composition of claim 1 wherein said analgesic, anti-inflammatory agent is D-phenylalanine.

3. The composition of claim 1 wherein said analgesic, anti-inflammatory agent is DL-phenylalanine.

4. The composition of claim 1 wherein said analgesic, anti-inflammatory agent is D-leucine.

5. The composition of claim 1 wherein said analgesic, anti-inflammatory agent is DL-leucine.

6. The composition of claim 2 wherein said D-phenylalanine is present in an amount of from 100 to 750 mg per unit dose.

7. An analgesic composition in oral unit dosage form comprising a therapeutically effective amount of D-phenylalanine or DL-phenylalanine and a synergistically effective amount of acetaminophen.

8. The analgesic composition of claim 7 comprising from 100 to 750 mg per unit dose of D-phenylalanine and from 100 to 500 mg per unit dose of acetaminophen.

* * * * *